US00PP33563P2

(12) United States Plant Patent
Zemzami

(10) Patent No.: US PP33,563 P2
(45) Date of Patent: Oct. 19, 2021

(54) MANDARIN TREE NAMED 'STAR COTT 1'

(50) Latin Name: *Citrus reticulata*
Varietal Denomination: Star Cott 1

(71) Applicant: Qualiagro SA, Casablanca (MA)

(72) Inventor: Mustapha Zemzami, Kenitra (MA)

(73) Assignee: Qualiagro SA, Casablanca (MA)

( * ) Notice: Subject to any disclaimer, the term of this patent is extended or adjusted under 35 U.S.C. 154(b) by 0 days.

(21) Appl. No.: 17/031,295

(22) Filed: Sep. 24, 2020

(51) Int. Cl.
*A01H 6/78* (2018.01)
*A01H 5/08* (2018.01)

(52) U.S. Cl.
USPC ..... Plt./201

(58) Field of Classification Search
USPC ..... Plt./156, 202, 201
See application file for complete search history.

(56) References Cited

PUBLICATIONS

Bulletin de la Protection des Obtentions Vegetales. 2017. http://www.onssa.gov.ma/images/controle_semences/bulletin-de-protection-des-obtentions-vegetales-n28-septembre-2017.pdf. 12 pages. (Year: 2017).*

* cited by examiner

*Primary Examiner* — Susan McCormick Ewoldt
*Assistant Examiner* — Karen M Redden
(74) *Attorney, Agent, or Firm* — Klarquist Sparkman, LLP

(57) ABSTRACT

A new and distinct mandarin tree characterized by low viable pollen, female sterility allowing production of seedless fruits, and earlier maturity.

8 Drawing Sheets

Genus and species: *Citrus reticulata.*
Variety denomination: 'Star Cott 1'.

CROSS-REFERENCE TO RELATED APPLICATIONS

Co-pending U.S. application Ser. No. 17/031,439 (Mandarin Tree named 'Star Cott 3') was developed by the same breeding program.

ORIGIN OF THE INVENTION

The present invention relates to a new and distinct variety of a mandarin tree named 'Star Cott 1', which was originated by the inventor by gamma irradiating the variety 'Nadorcott' (U.S. Plant Pat. No. 10,480), and selecting for trees having pronounced male and female sterility, desired maturity timeframe, and significant yield.

BACKGROUND OF THE INVENTION

The *Citrus* industry is facing tremendous challenges to cope with the recent extensive world-wide plantings of soft *Citrus*. This congested the market supply due to the narrow maturity windows of conventional varieties, especially clementine varieties, which suffer unprofitable sell prices that impact tremendously farmer's income. Mandarins provide a solution as a soft easy peeling *Citrus* fruit. However, the late maturity of mandarins does not completely fit in filling the gap of market supply shortage of mid-season from the end of November to the end of January. Furthermore, mandarins cause problems of cross-pollination, which are unacceptable to farmers as fruit seediness constitutes a major constraint to access better rewarding markets.

To overcome this problem, a breeding program was instituted to generate new varieties of non-cross-pollinating mandarins that can fill the gap of mid-season market supply with 'seedless/low-seeded' easy peeling *Citrus* fruits. The breeding program targeted creation of new varieties with both marked male and female sterility, with a range of maturity windows that are better adapted to the market. Budwood of 'Nadorcott' (U.S. Plant Pat. No. 10,480) was gamma irradiated in 2013 using a Cobal-60 panoramic irradiator in Boukhalef, Tangier, Morocco.

Irradiated budwood was sequentially grafted in the *Citrus* nursery at Kénitra, Morocco on Volkamer lemon root-stock (unpatented) to speed up growth. The last generation of vegetatively propagated plants was planted in 2015 at an experimental field in Beni Mellal, Morocco. Selection observations started in 2017 with a focus on marked male and female sterility, maturity timeframe, yield potential and other agronomic features of interest.

BRIEF SUMMARY OF THE INVENTION

The objective was substantially achieved, along with other desirable improvements, as evidenced by the following unique combination of characteristics that are outstanding in the new variety and that distinguish it from 'Nadorcott', as well as from all other varieties of which I am aware. Among several selections, 'Star Cott 1' has several distinct characteristics that make it unique as compared to 'Nadorcott', including but not limited to:

1. Low viable pollen as shown by pollen culture on sucrose-Agar medium (6.5% for 'Star Cott 1' compared to more than 60% for 'Nadorcott').
2. Pronounced female sterility allowing production of very low-seeded fruits (less than 1 seed/fruit for 'Star Cott 1' vs more than 13 seeds/fruit for 'Nadorcott') under heavy open field cross-pollination.

3. Maturity of 'Star Cott 1' is 6 to 7 weeks prior to 'Nadorcott' (week 48 for 'Star Cott 1' vs week 2 for 'Nadorcott') in Beni Mellal, Morocco (Northern Hemisphere).

'Star Cott 1' also has several distinct characteristics from 'Star Cott 3', including but not limited to:

1. 'Star Cott 1' has numerous branches and dense vegetation with numerous long and narrow leaves, while 'Star Cott 3' has thinner vegetation with elongated branches and large leaves.
2. Early ripening time (weeks 48 to 52 for 'Star Cott 1' vs weeks 4 to 9 for 'Star Cott 3' in the northern hemisphere).

Asexual reproduction of this new variety by bud-grafting, as performed in the *Citrus* nursery at Kénitra, Morocco, shows that the foregoing and all other characteristics and distinctions come true to form and are established and transmitted through succeeding propagations. Bud-eyes are collected and side grafted on a certified receptive Volkamer lemon root-stock and grown for development under plastic house covered with a layer of anti-insect white screen and a top layer of anti-UV yellow plastic. Grafting, development and maintenance of plants were performed at the *Citrus* nursery in Kénitra, Morocco. Each of the progeny exhibits identical characteristics to the original plant. The present invention has not been evaluated under all possible environmental conditions. The phenotype may change with variations in environment without a change in the genotype of the plant.

BRIEF DESCRIPTION OF THE DRAWINGS

The accompanying illustrations show typical specimens of the tree, flowers, and fruit of 'Star Cott 1' depicted in color as nearly true as it is reasonably possible to make the same in a color illustration of this character.

'Star Cott 1' is indicated in photograph illustrations as 'Super Cott 1', which was the prior variety name of 'Star Cott 1'.

DETAILED BOTANICAL DESCRIPTION

The following is a detailed description of my new mandarin tree selection 'Star Cott 1' with color descriptions using terminology in accordance with The Royal Horticultural Society (London) Colour Chart, $4^{th}$ Edition, (2001), except where ordinary dictionary significance of color is indicated. Observations were made of a 5-year old tree.

Tree:

*Plant diameter.*—230 cm on a 4 year old tree on *Citrus volkameriana* root-stock.

Figure 2:
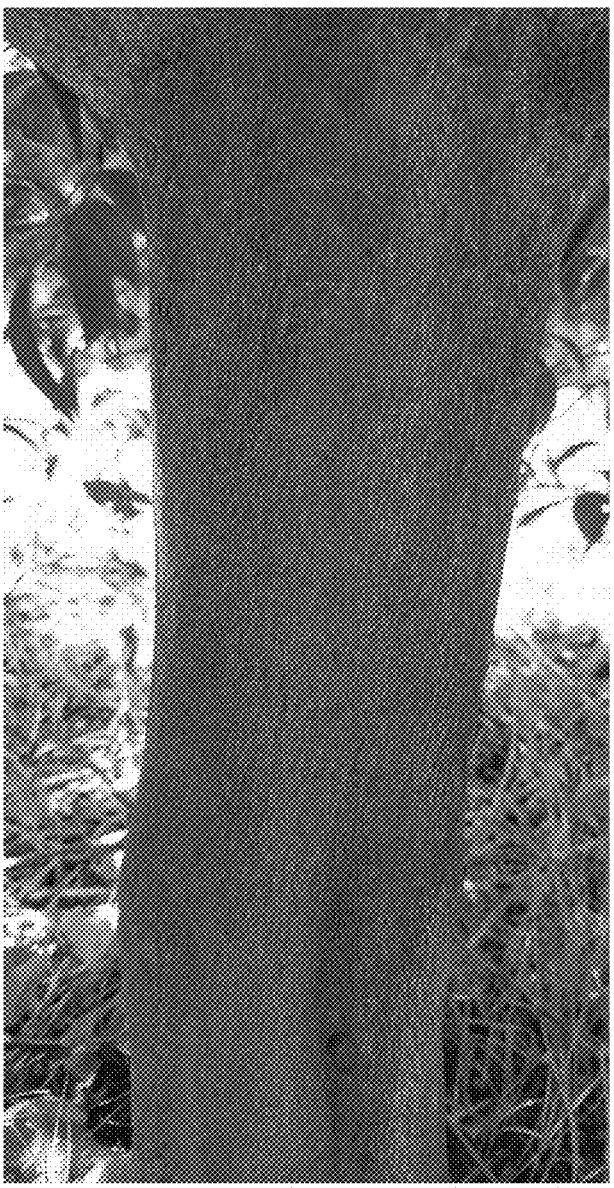
FIG. 2 is a photograph of 'Star Cott 1' trunk showing that the stem is strong with smooth bark. It is equal in diameter to the root-stock.

*Trunk.*—Variety stem is firm with a smooth bark; its diameter is equal to the root-stock. See FIG. 2.

Figure 1:
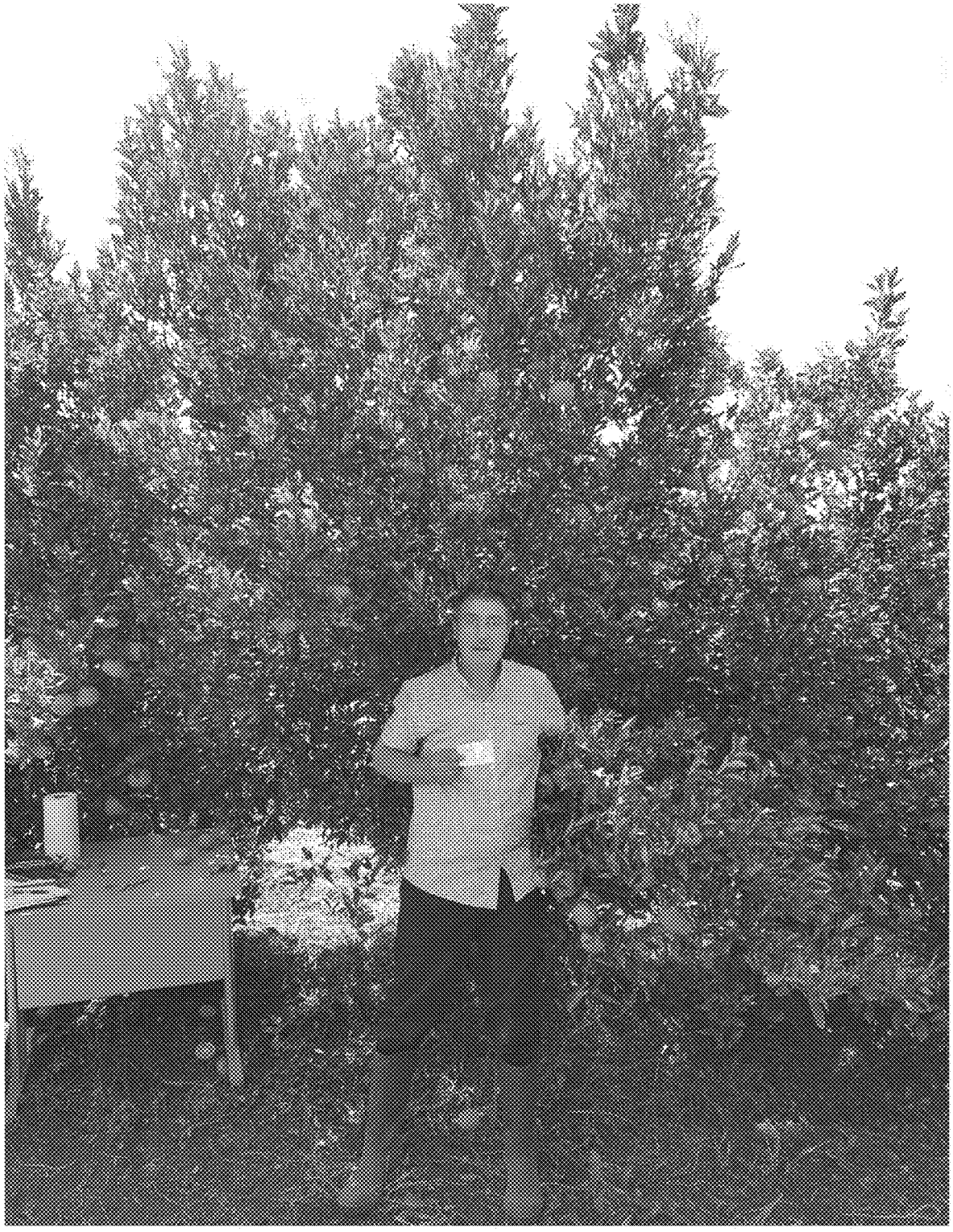
FIG. 1 is a photograph of 'Star Cott 1' tree canopy with the upright growth.

*Canopy.*—Vigorous vegetation with marked upright growth resulting in an ellipsoid shape. The density of branches is high; their attachment angle is narrow. See FIG. 1.

Figure 3:
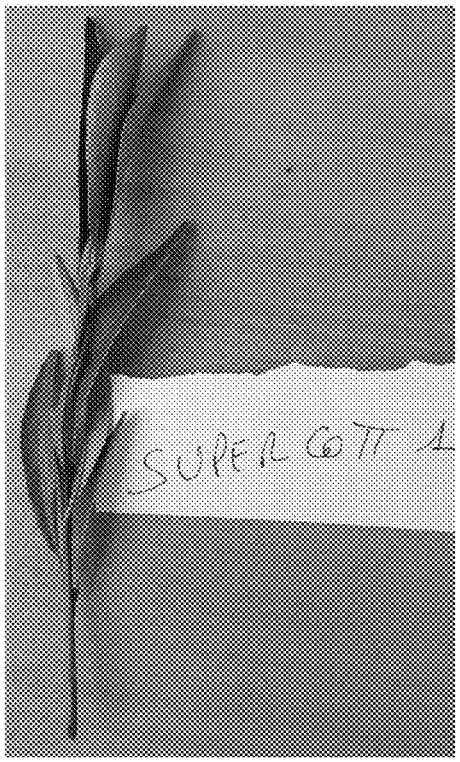
FIG. 3 is a photograph of a 'Star Cott 1' first year twig, which is green, glabrous, and thin.
Figure 4:
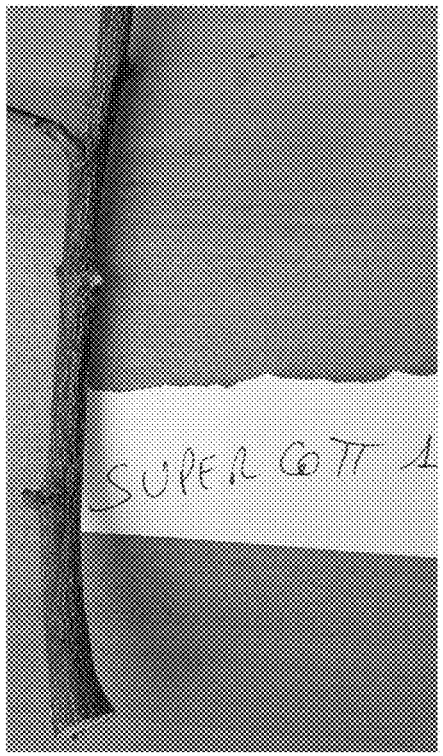
FIG. 4 is a photograph of a 'Star Cott 1' second year twig, which is striate.
Figure 5:
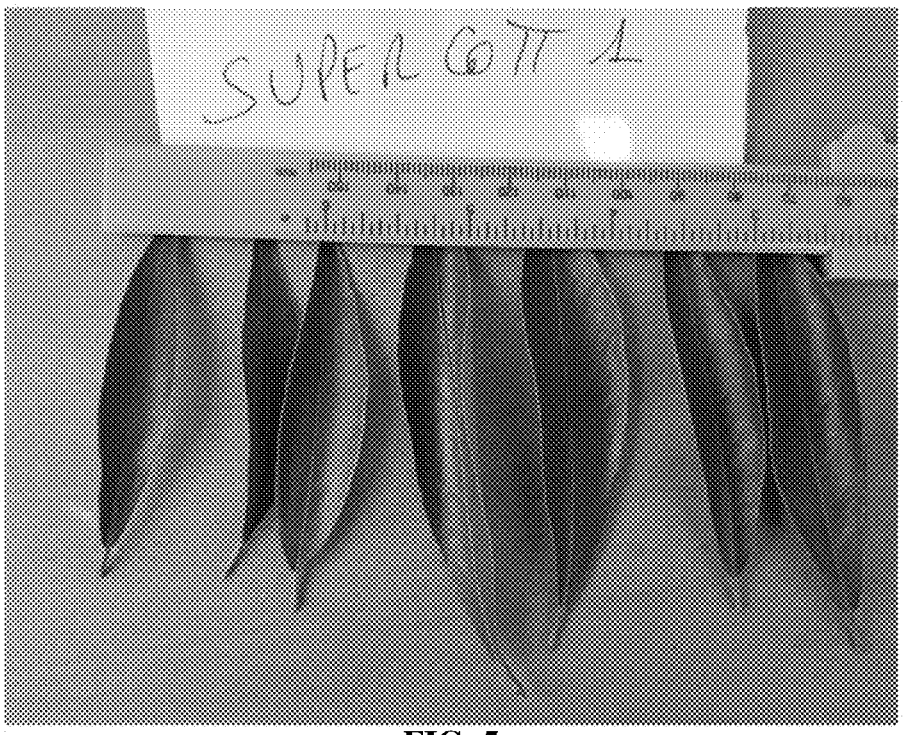
FIG. 5 is a photograph of 'Star Cott 1' leaves.
Figure 6:
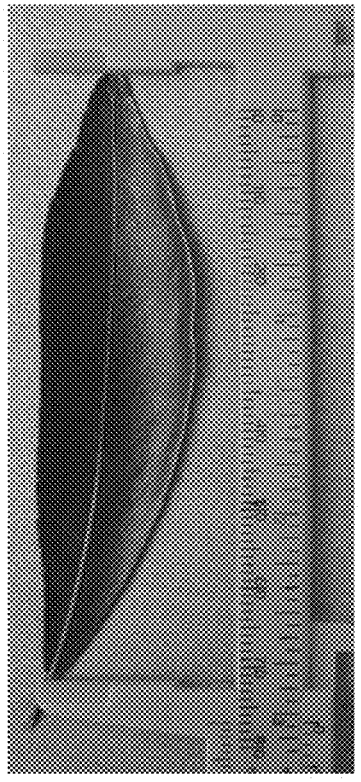
FIG. 6 is a photograph of a 'Star Cott 1' leaf, showing lanceolate and crenate shape.
Figure 7:
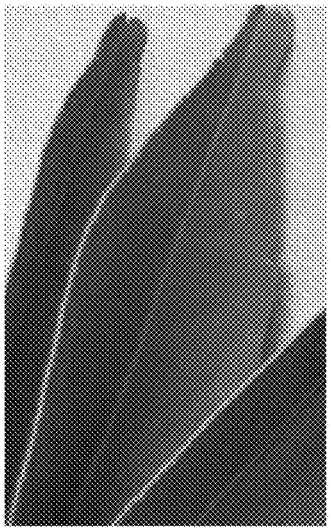
FIG. 7 is a photograph of a 'Star Cott 1' leaf, showing apex slightly emarginated.
Figure 8:
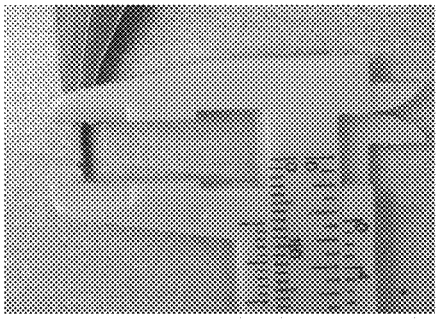
FIG. 8 is a photograph of a 'Star Cott 1' petiole, showing it is glabrous with no wings.
Figure 9:
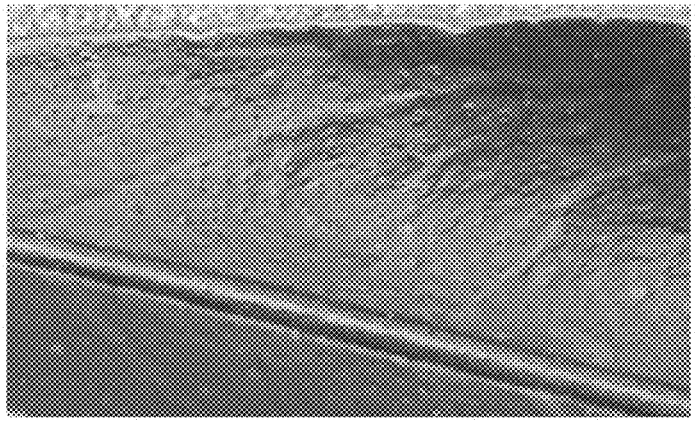
FIG. 9 is a photograph of a 'Star Cott 1' leaf, showing conspicuous oil glands.
Figure 10:
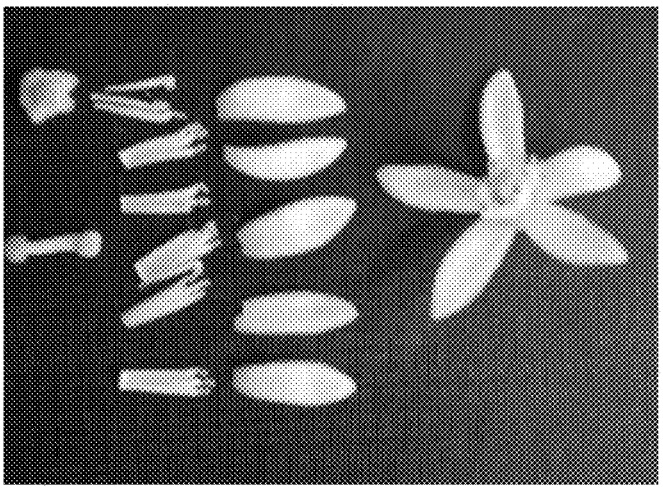
FIG. 10 is a photograph of 'Star Cott 1' flowers with five petals.
Figure 11:
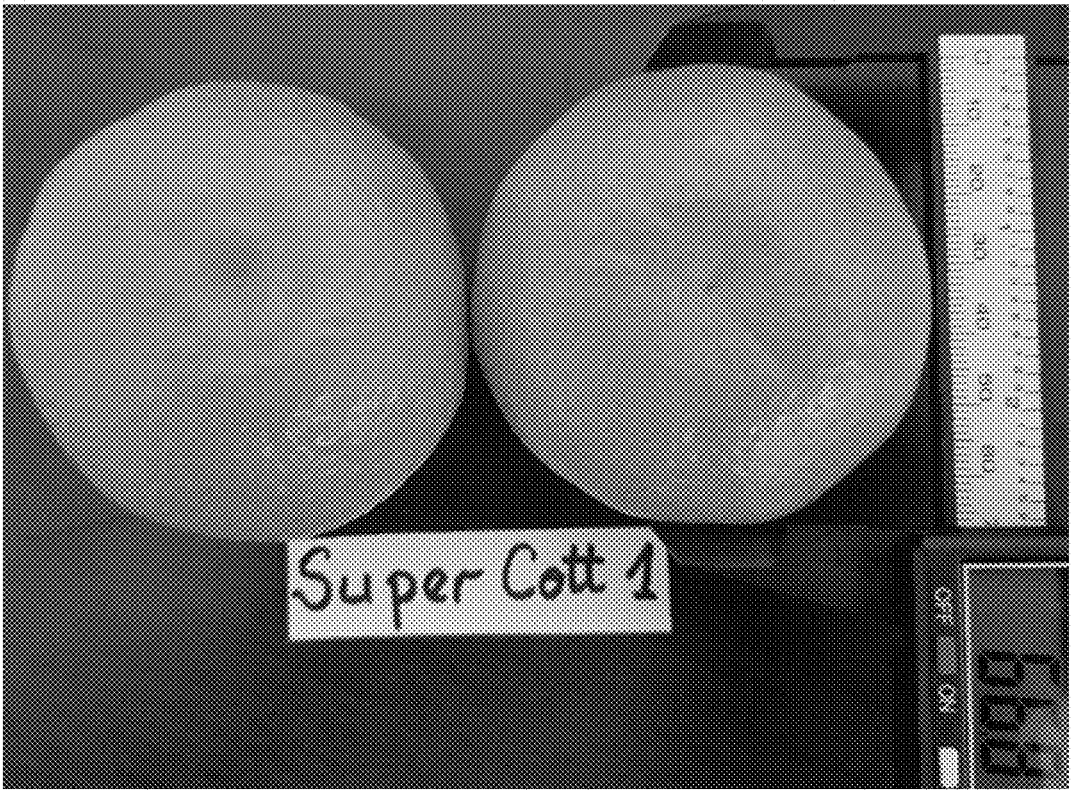
FIG. 11 is a photograph of a 'Star Cott 1' fruit, having a width of about 67 mm, with an areola that is usually obvious with a tiny stylar scar.
Figure 12:
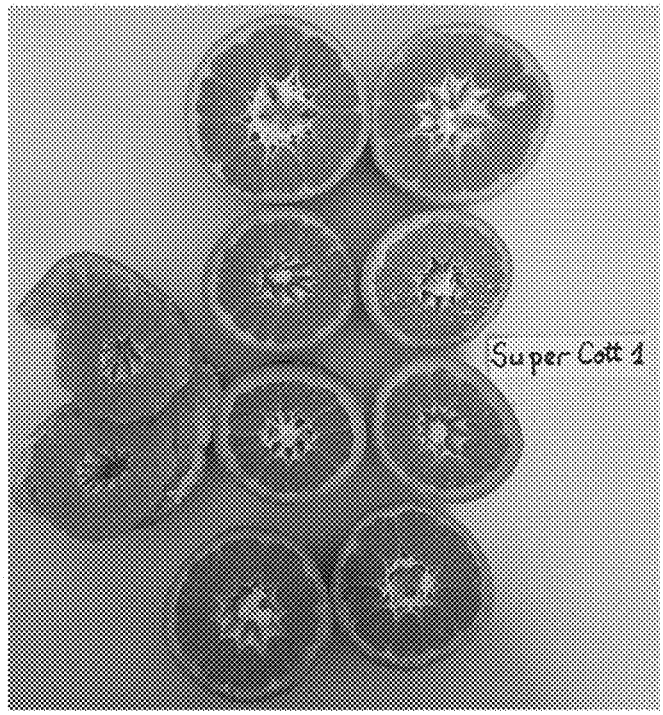
FIG. 12 is a photograph of a 'Star Cott 1' fruit, showing the inside. 'Star Cott 1' has less than 1 seed/fruit and 9 to 11 segments.
Figure 13:
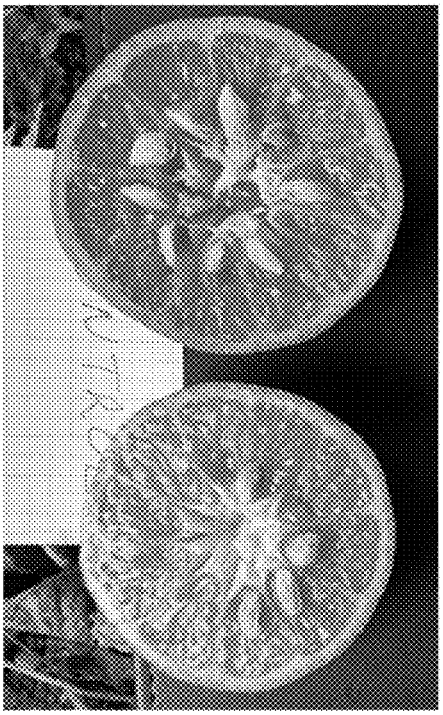
FIG. 13 is a photograph of a 'Nadorcott' fruit, for a comparison. 'Nadorcott' has about 13 seeds)/fruit and 9 to 12 segments.
Figure 14:
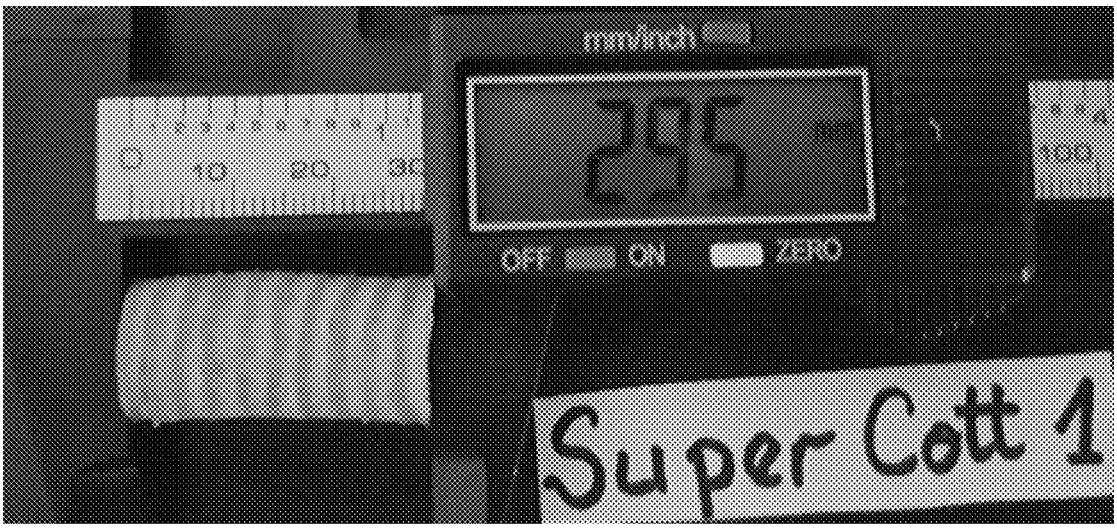
FIG. 14 is a photograph of a 'Star Cott 1' fruit peel, with a thickness of 3 mm.
Figure 15:
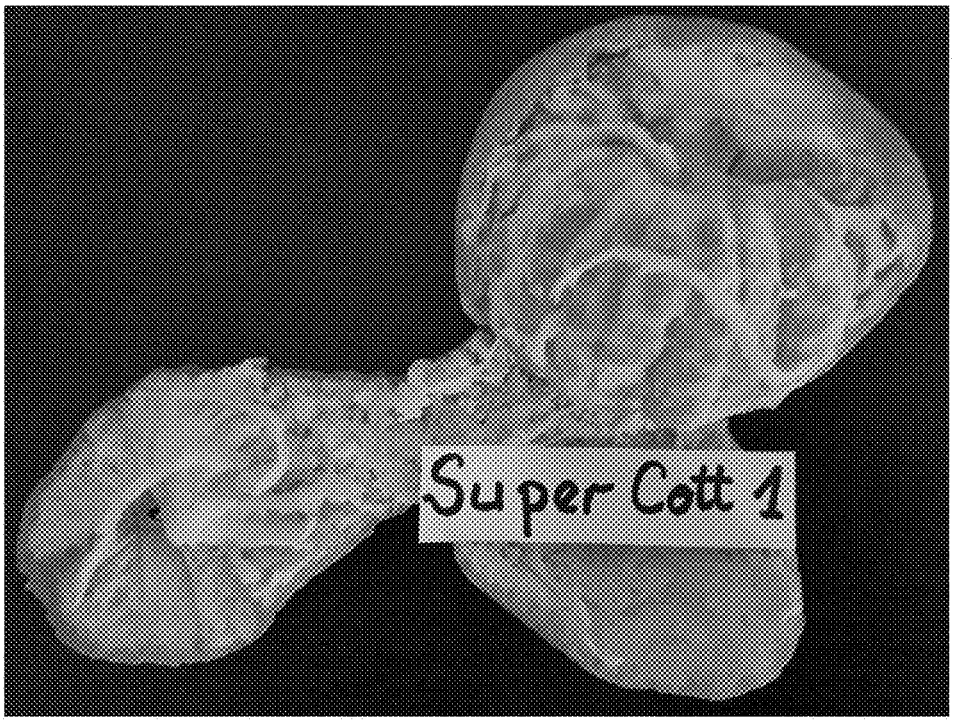
FIG. 15 is a photograph of a 'Star Cott 1' fruit, showing that it is an easy peeling fruit, and presence of medium albedo strands.
Figure 16:
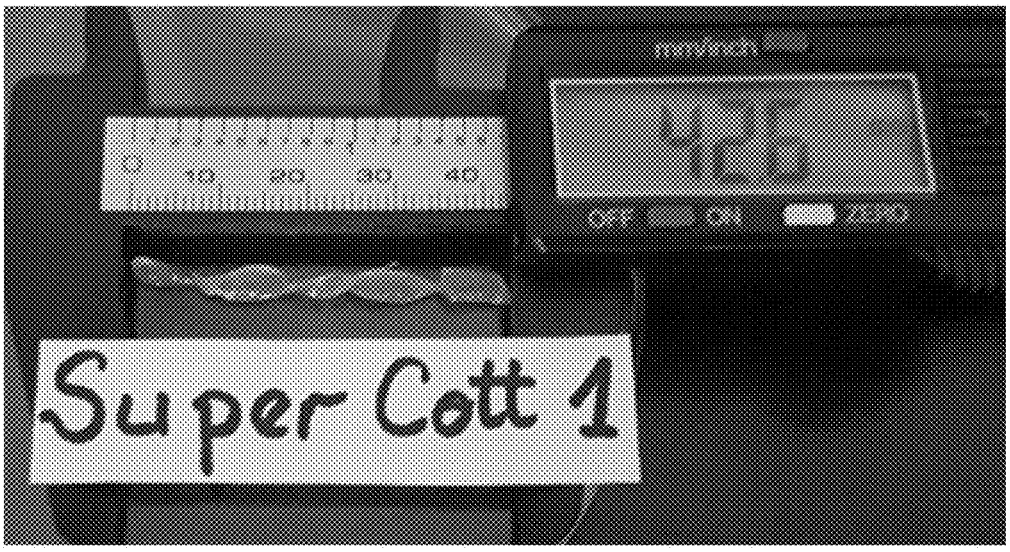
FIG. 16 is a photograph of a 'Star Cott 1' fruit juice bag length of 8.5 mm.
Figure 17:
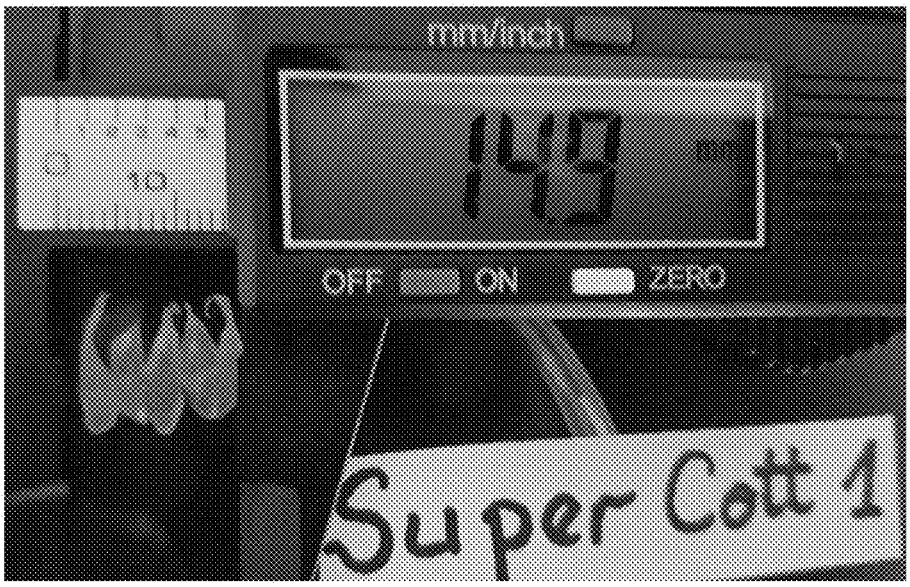
FIG. 17 is a photograph of a 'Star Cott 1' fruit juice bag width of 3 mm.
Figure 18:
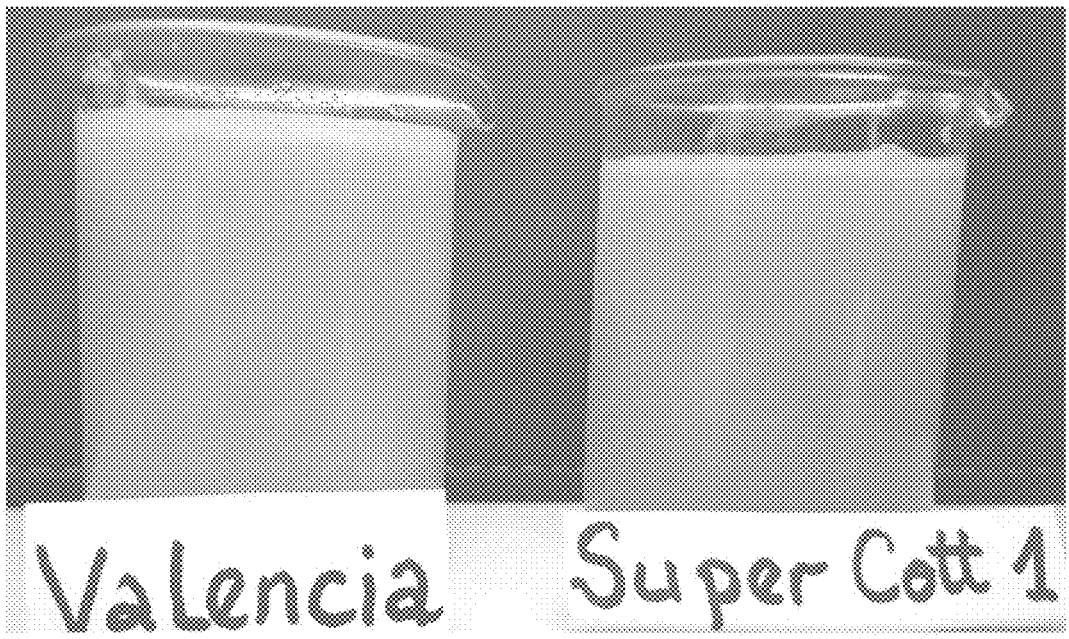
FIG. 18 is a photograph comparing juice from late Valencia and 'Star Cott 1' fruit.

*Twig.*—First year twig is glabrous, moderately thick and has a green color. See FIG. 3. It becomes subsequently striate with age. See FIG. 4. No thorns and no spines.

*Growth conditions.*—No particular farming techniques are needed to grow 'Star Cott 1'. It does not require any special conditions beside what is usually applied for *Citrus* production.

Stem description:

*Stem length.*—740 mm.

*Diameter.*—108 mm.

*Texture.*—Smooth.

*Strength.*—Strong.

*Color.*—RHS N 197 B Light Olive Gray.

Leaf description: Unifoliate with an entire margin, it is lanceolate in shape and moderately conduplicate with a glabrous non-winged petiole. The lamina has an obtuse apex slightly emarginated.

*Shape.*—Lanceolate.

*Length.*—76 mm.

*Width.*—23 mm.

*Apex.*—Obtuse with slight emargination.

*Margin.*—Entire.

*Texture* (*both surfaces*).—Glabrous.

*Color.*—Adaxial: RHS 131 B (Dark Green); Abaxial: RHS 131 C (Moderate Green).

*Petiolate or sessile.*—Petiolate. Petiole length: 7 mm. Petiole diameter: 0.8 mm. Petiole color: RHS 134 B (Slightly Yellow Green).

Root description: Grafted on *Citrus volkameriana* rootstock.

Flowers: Single type of flower mostly in clusters but single flowers at the tip of a leafy bud are also present. Like 'Nadorcott', 'Star Cott 1' flowers in mid-March and its flowering is intense.

*Height.*—12 mm.

*Diameter.*—7.3 mm before anthesis.

*Typical date of bloom.*—Mid-March in Beni Mellal, Morocco.

*Number of flowers.*—1 type in singles and clusters.

*Color.*—RHS 155 D (Yellowish White).

*Pedicel.*—8 to 10 mm in length.

*Calyx.*—5 mm in diameter with 5 sepals arranged in a cup-like structure.

*Sepal.*—Isosceles triangular shape measuring 3.5 mm at the base and 2.5 mm on the side.

*Corolla.*—Composed of 5 petals (14.5 mm in length and 5.0 mm width) arranged in a circle in alternation with the sepals.

*Stamens.*—About 20 in number that stick together, arranged in a circle around the pistil and their anthers are positioned around the stigma at about the same height.

Rostellum:

*Length.*—8.2 mm.

*Thickness.*—1.1 mm.

*Color.*—RHS 154 D (Light Yellow Green).

Fruit: Fruit attachment to the stalk is strong with sometimes short radial grooves which are not always conspicuous. No neck is present.

*Shape.*—Slightly larger than longer and has an obloid form.

*Distal end.*—Slightly depressed, areola usually present.

*Diameter at equatorial level.*—65 mm and it is truncate at both stalk and distal parts.

*Width.*—63 mm.

*Texture.*—Smooth.

*Color.*—Green fruit — RHS 126 A (medium blue Green); non-dehiscent fruit — RHS 32 C (slightly reddish Orange).

*Fruit rind.*—Slightly reddish Orange in color RHS 32 C, and has a thickness of about 2.95 mm shared equally by flavedo and albedo. The rind is dotted with oil glands of about 1 mm in diameter at a density of about 30 glands per $cm^2$, and about twice as much tiny oil glands (about $60/cm^2$). The albedo is of pinkish White color RHS N155 B.

*Segments.*—9 to 11 which are uniform with a thin membrane.

*Seeds.*—Less than 1 seed per fruit on average. Mean seed count under high cross pollination pressure in mixed bloc with 'Nadorcott', Rough lemon and Clementine in adjacent rows was 0.8 seed per fruit. Seeds are polyembryonic and seed-coat is of yellowish-White color RHS 155 D.

*Fruit axis.*—Hollow with a diameter of about 8 mm.

*Peel thickness.*—3 mm. Fruit is easy peeling with medium albedo strands present. A tiny stylar scar is visible.

*Navel.*—No navel is visible when the fruit is peeled.

*Pulp.*—Strong reddish orange color — RHS 31A, it is soft and juicy. Juice vesicles are delicate rolls of 8.5 mm long and 3 mm large. The percentage of juice in the endocarp exceeds 50%, Total Soluble Solids (TSS) varies from 10 to 13% and Titratable Acidity (TA) varies from about 12 to 0.75% acidity between start to end of maturity.

Production: 5-year old planting with a spacing of 6 by 2 m produces over 50 metric tons per ha.

Tolerance to heat waves: 'Star Cott 1' is similar to the mother variety 'Nadorcott', which is relatively tolerant to mid-spring heat waves that occur in the Mediterranean Basin.

Tolerance to frost: 'Star Cott 1' is similar to the mother variety 'Nadorcott', which is resistant to mild negative temperatures (0 to −3° C.) if the duration does not exceed 1 to 2 hours. If this range of negative temperatures is recorded for several consecutive days, or if temperatures decline below −3° C., the fruit is affected by reduction of juice content and irreversible skin damage, especially fruits of the outer side of the canopy.

Disease resistance: No trials have been conducted, however, 'Star Cott 1' does not seem to be sensitive to *Alternaria*.

Market use: Fruit of 'Star Cott 1' is intended mainly for fresh fruit consumption, as it is the case for the product of 'Nadorcott', which is well appreciated worldwide.

I claim:

1. A new and distinct mandarin tree named 'Star Cott 1', as herein shown and described.

* * * * *